United States Patent
Heinrich et al.

(10) Patent No.: US 9,829,468 B2
(45) Date of Patent: Nov. 28, 2017

(54) METHOD AND DEVICE FOR DETECTING DEFECTS WITHIN A TEST OBJECT

(71) Applicant: SIEMENS AKTIENGESELLSCHAFT, München (DE)

(72) Inventors: Werner Heinrich, Oberkrämer OT Bärenklau (DE); Hubert Mooshofer, München (DE)

(73) Assignee: SIEMENS AKTIENGESELLSCHAFT (DE)

(*) Notice: Subject to any disclaimer, the term of this patent is extended or adjusted under 35 U.S.C. 154(b) by 778 days.

(21) Appl. No.: 14/370,651

(22) PCT Filed: Dec. 28, 2012

(86) PCT No.: PCT/EP2012/077013
§ 371 (c)(1),
(2) Date: Jul. 3, 2014

(87) PCT Pub. No.: WO2013/104525
PCT Pub. Date: Jul. 18, 2013

(65) Prior Publication Data
US 2015/0057953 A1 Feb. 26, 2015

(30) Foreign Application Priority Data
Jan. 12, 2012 (DE) .......... 10 2012 200 409

(51) Int. Cl.
*G01N 29/44* (2006.01)
*G01N 29/22* (2006.01)
(Continued)

(52) U.S. Cl.
CPC ......... *G01N 29/221* (2013.01); *G01N 29/043* (2013.01); *G01N 29/069* (2013.01);
(Continued)

(58) Field of Classification Search
USPC .......................................... 702/39
See application file for complete search history.

(56) References Cited

U.S. PATENT DOCUMENTS

| 4,481,822 A | 11/1984 | Kubota et al. |
| 4,694,434 A | 9/1987 | von Ramm et al. |

(Continued)

FOREIGN PATENT DOCUMENTS

| CN | 101135672 A | 3/2008 |
| CN | 101711358 A | 5/2010 |

(Continued)

OTHER PUBLICATIONS

Chinese Office Action, dated Sep. 6, 2015, issued in corresponding Chinese Patent Application No. 201280066799.3. Includes English translation. Total 11 pages.
(Continued)

*Primary Examiner* — Paul D Lee
(74) *Attorney, Agent, or Firm* — Ostrolenk Faber LLP (57) ABSTRACT

A device and a method for detecting at least one defect in a test object (2). At least one test head (1) radiates an ultrasonic signal at different measuring points (MP) into the test object (2) with each point at an insonation or radiation angle (α) in order to ascertain multiple measurement data sets (MDS). The angle is constant for each data set (MDS). An analyzing unit (4) carries out an SAFT (Synthetic Aperture Focusing Technique) analysis for each ascertained measurement data set (MDS) using a common reconstruction grid (RG) inside the test object (2) in order to calculate an SAFT analysis result for each measurement data set (MDS). The analyzing unit (4) superimposes the calculated SAFT analysis results in order to calculate an orientation-independent defect display value ($S_{RP}$) for each reconstruction point (RP) of the common reconstruction grid (RG).

16 Claims, 4 Drawing Sheets (51) Int. Cl.
*G01N 29/06* (2006.01)
*G01N 29/26* (2006.01)
*G01N 29/265* (2006.01)
*G01N 29/32* (2006.01)
*G01N 29/04* (2006.01)

(52) U.S. Cl.
CPC ......... *G01N 29/262* (2013.01); *G01N 29/265* (2013.01); *G01N 29/4427* (2013.01); *G01N 29/041* (2013.01); *G01N 29/32* (2013.01); *G01N 29/4418* (2013.01); *G01N 2291/044* (2013.01)

(56) References Cited

U.S. PATENT DOCUMENTS

| | | |
|---|---|---|
| 5,549,002 A | 8/1996 | Howard et al. |
| 5,993,393 A * | 11/1999 | Ryan ................ G01S 7/52028 600/447 |
| 8,656,782 B2 | 2/2014 | Boehm ........................ 73/620 |
| 2008/0121040 A1 * | 5/2008 | MacLauchlan ...... G01N 29/265 73/618 |
| 2009/0279772 A1 * | 11/2009 | Sun ..................... G06K 9/6298 382/141 |
| 2010/0212431 A1 | 8/2010 | Clossen-Von Lanken Schulz et al. |

FOREIGN PATENT DOCUMENTS

| | | |
|---|---|---|
| DE | 44 16 829 A1 | 11/1995 |
| DE | 10 2008 023 862 A1 | 11/2009 |
| EP | 2 051 070 A1 | 4/2009 |
| EP | 2 120 045 A1 | 11/2009 |
| WO | WO 2008/138684 A1 | 11/2008 |

OTHER PUBLICATIONS

International Search Report dated Apr. 8, 2013 issued in corresponding International Application No. PCT/EP2012/077013.
Written Opinion dated Apr. 8, 2013 issued in corresponding International Application No. PCT/EP2012/077013.

* cited by examiner

$$S_{RP} = \sum_{i=1}^{M} g_i SAFT(MDS_i)$$

METHOD AND DEVICE FOR DETECTING DEFECTS WITHIN A TEST OBJECT

CROSS-REFERENCE TO RELATED APPLICATIONS

The present application is a 35 U.S.C. §§371 national phase conversion of PCT/EP2012/077013, filed Dec. 28, 2012, which claims priority of German Patent Application No. 102012200409.2, filed Jan. 12, 2012, the contents of which are incorporated by reference herein. The PCT International Application was published in the German language.

TECHNICAL FIELD

The invention relates to a method and a device for detecting at least one defect within a test object, and in particular to orientation-independent defect detection by means of ultrasound.

TECHNICAL BACKGROUND

After their production, test objects, for example machine components, are tested to find out whether they have defects, for example small cavities or cracks. The testing is preferably carried out by means of ultrasound. For ultrasound testing, the so-called SAFT (Synthetic Aperture Focusing Technique) method is known for detecting small defects within the test object and distinguishing them from other defects. The SAFT method is used to increase the spatial resolution, in order to obtain accurate information about the position and the shape of reflecting defects within the test object. In order to reliably detect reflecting defects within the test object, test heads with an aperture angle which is as wide as possible are used in the SAFT method. Furthermore, the SAFT method exhibits the greatest effect with a wide aperture angle.

Figure 1:
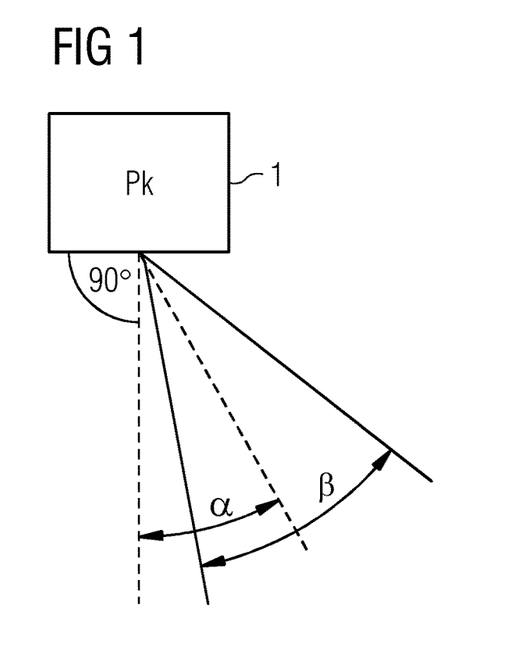
FIG. 1 shows a diagram to represent an insonation angle and an aperture angle in the case of an ultrasound test head such as may be used in the method according to the invention and in the device according to the invention.

FIG. 1 schematically shows a test head PK, which insonates sound signals with an insonation angle α into the test object, and which has an aperture angle β. The wide aperture angle β means that the test head PK has a small diameter, and is ideally almost point-like. The aperture angle β of the sonic beam is limited by the fact that a sufficient amount of energy must be introduced into the component to be tested, i.e. the test object, particularly in the case of long sound paths. The greater the aperture angle β is, the smaller the amount sound energy introduced is—owing to the smaller transducer area—and the greater the energy distribution of the insonated ultrasound signal is, and the more weakly it is reflected back by defects as an echo sound signal, so that the signal-to-noise ratio SNR decreases.

DE 10 2008 023 862 A1 describes a device and a method for generating an ultrasound image. Series of measurements, which are recorded by a group radiator, are evaluated by means of an SAFT algorithm. This conventional method, besides the necessary use of a group radiator, presupposes that a plurality of insonation directions, or insonation angles, belonging to a measurement series can be measured from the same insonation position, or measurement position. In DE 10 2008 023 862 A1, a group radiator test head is placed at different locations, or positions, on a surface of a test object, so that a respective measurement series is assigned to a particular measurement position on the test object. Subsequently, at each of the measurement positions, insonation is carried out with different insonation angles α. For each insonation angle, an image is generated.

However, the method described in DE 10 2008 023 862 A1 has some disadvantages. In this conventional method, it is not possible to work with a single-oscillator test head which has a fixed insonation angle. In existing test systems, however, single-oscillator test heads with a fixed insonation angle are often used. Furthermore, the conventional method is restricted to the use of group radiators and to carrying out measurements in the same positions. Furthermore, this conventional method does not allow continuous movement of the ultrasound test heads during the testing, that is to say the ultrasound test heads cannot be moved uniformly over the component, or the test object, so that a position offset occurs between a plurality of insonations.

SUMMARY OF THE INVENTION

It is therefore an object of the present invention to provide a method and a device for detecting at least one defect within a test object, which avoids the aforementioned disadvantages but nevertheless delivers a detection signal with a high signal-to-noise ratio.

This object is achieved according to a method according to the invention.

Accordingly, the invention provides a method for detecting at least one defect within a test object, comprising the steps:
determining a plurality of measurement data sets of the test object,
an ultrasound signal respectively being insonated at various measurement points into the test object with a selected preferably constant insonation angle used at all of the measurement points in order to determine a measurement data set. This insonation angle is varied for each measurement data set for the determination of the measurement data sets;
carrying out an SAFT (Synthetic Aperture Focusing Technique) evaluation for each measurement data set determined, by using a common reconstruction grid RG within the test object for calculating an SAFT evaluation result for each measurement data set; and
superposing the calculated SAFT evaluation results, in order to calculate an orientation-independent defect display value for each reconstruction point of the reconstruction grid.

The method according to the invention offers the advantage that it makes it possible to increase the angle range for the SAFT evaluation method, without being restricted to use of group radiators and/or to carrying out measurements at the same measurement positions.

In one possible embodiment, the number of measurement points is not the same for all measurement data sets.

In one possible embodiment of the method according to the invention, the calculated SAFT evaluation results of the measurement data sets determined are weighted in order to level the amplitude level before the superposition of the SAFT evaluation results.

In one possible embodiment of the method according to the invention, the superposed SAFT evaluation results are rectified, and smoothed by lowpass filtering.

In another possible embodiment of the method according to the invention, the measurement positions lie in a measurement network on the surface of the test object.

In another possible embodiment of the method according to the invention, before the determination of the measurement data sets, the measurement positions are adjusted by means of an adjustment reflector with the aid of a reflected echo signal of the adjustment reflector.

In another possible embodiment of the method according to the invention, in order to determine a measurement data set of the test object, an ultrasound signal is insonated by means of a single-oscillator test head or by means of a group radiator at various measurement points into the test object with the insonation angle respectively set for the determination of the measurement data set.

In this case, it is possible to use either single-oscillator test heads with an adapter wedge (for adjusting the insonation angle), and single-oscillator test heads which are designed for a particular insonation angle.

In one possible embodiment of the method according to the invention, the analog echo ultrasound signals reflected by the test object for the various measurement points are amplified and subsequently digitized to form echo signals assigned to measurement points, which form the measurement data set of the test object.

In one possible embodiment of the method according to the invention, the test head or the group radiator for insonating the ultrasound signal and for recording the echo ultrasound signal is moved continuously over the surface of the test object.

In one possible embodiment of the method according to the invention, the SAFT evaluation results, calculated for the various insonation angles, of the various measurement data sets for the associated respective insonation angle are stored separately and are selected for the superposition with the aid of the insonation angle.

In one possible embodiment of the method according to the invention, the ultrasound signal is insonated into the test object as a longitudinal wave and/or transverse wave.

In another possible embodiment of the method according to the invention, the calculated defect display values of the reconstruction grid are displayed to a tester two-dimensionally in sectional views or three-dimensionally on a display.

In another possible embodiment of the method according to the invention, the calculated defect display values of the examined test object are respectively compared with setpoint values of a stored model of the test object to be examined, in order to calculate difference values which indicate a defect of the test object when predetermined tolerance threshold values are exceeded.

In another possible embodiment of the method according to the invention, a test object identified as defective is automatically rejected.

The invention furthermore provides a device for detecting at least one defect within a test object, the device having the features disclosed herein.

Accordingly, the invention provides a device for detecting at least one defect within a test object, comprising: at least one test head for insonating an ultrasound signal at various measurement points into the test object with an insonation angle in order to determine a plurality of measurement data sets, wherein in order to determine each measurement data set, the ultrasound signal is respectively insonated with an associated insonation angle into the test object at the respective measurement points for the measurement data set, and which angle is varied for each measurement data set for the determination of the measurement data sets; and comprising an evaluation unit which carries out an SAFT (Synthetic Aperture Focusing Technique) evaluation for each measurement data set determined, by using a common reconstruction grid within the test object for calculating an SAFT evaluation result for each measurement data set, the evaluation unit superposing the calculated SAFT evaluation results, in order to calculate an orientation-independent defect display value for each reconstruction point of the common reconstruction grid.

In one possible embodiment of the device according to the invention, the calculated SAFT evaluation results of the measurement data sets determined are weighted by means of the evaluation unit, in order to level the amplitude level before the superposition of the SAFT evaluation results.

In one possible embodiment of the device according to the invention, the test head can be moved continuously relative to a surface of the test object in order to determine the measurement data sets.

Possible embodiments of the device according to the invention and of the method according to the invention for detecting at least one defect within a test object will be explained in more detail below with reference to the appended figures, in which:

FIG. 1 schematically shows a test head, or ultrasound test head, 1, which may be used in the method according to the invention and in the device according to the invention. The ultrasound test head 1 has an insonation angle α for insonating ultrasound signals into a test object 2, the ultrasound signal being insonated in an aperture angle β. The insonation angle α of a test head 1 may, for example, be modified with the aid of wedges which are clamped between the test head 1 and the test object 2. Furthermore, the insonation angle may be modified by time-offset driving of the test head 1, if the test head 1 is a group radiator.

Figure 2:
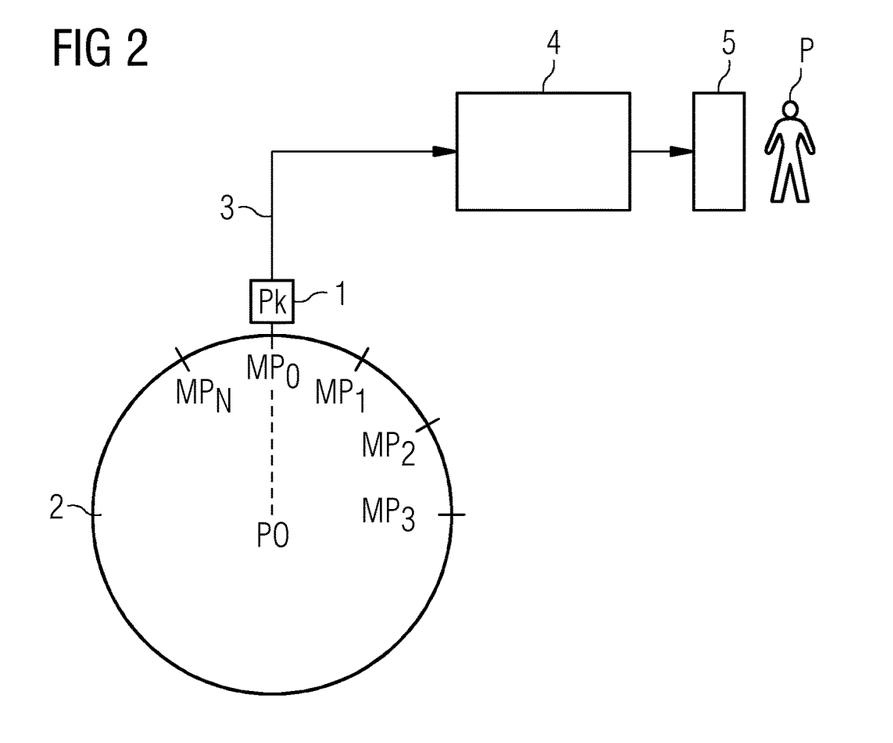
FIG. 2 shows a diagram to explain the functionality of the method according to the invention and of the device according to the invention for detecting defects within a test object.

FIG. 2 schematically shows an exemplary embodiment of the device according to the invention for detecting at least one defect within a test object 2. In the example represented, the test object 2 is cylindrical, or rotationally symmetrical. The position of the test head 1 relative to the test object 2 can be modified. On the one hand, it is possible for the test head 1 to be moved along the surface of the test object 2. Alternatively, the test object 2 may also be moved relative to the test head 1, for example by the test object 2, which is represented as rotationally symmetrical in FIG. 2, being rotated, or turned, about an axis. In this way, the test head 1 reaches various measurement points MP, as represented in FIG. 2. The test head 1 is used to insonate an ultrasound signal at various measurement points MP into the test object 2 with an insonation angle α, at all of the measurement points in each measurement data set MDS in order to determine a plurality of measurement data sets MDS. In order to determine a measurement data set MDS, the ultrasound signal is respectively insonated with a particular associated insonation angle α for the measurement data set into the test object 2. In order to determine different measurement data sets MDS, the insonation angle α is varied for each measurement data set MDS. The recorded time-based signals are transmitted via a signal line 3 to an evaluation unit 4, to which a display unit 5 for a tester P is connected.

Figure 3:
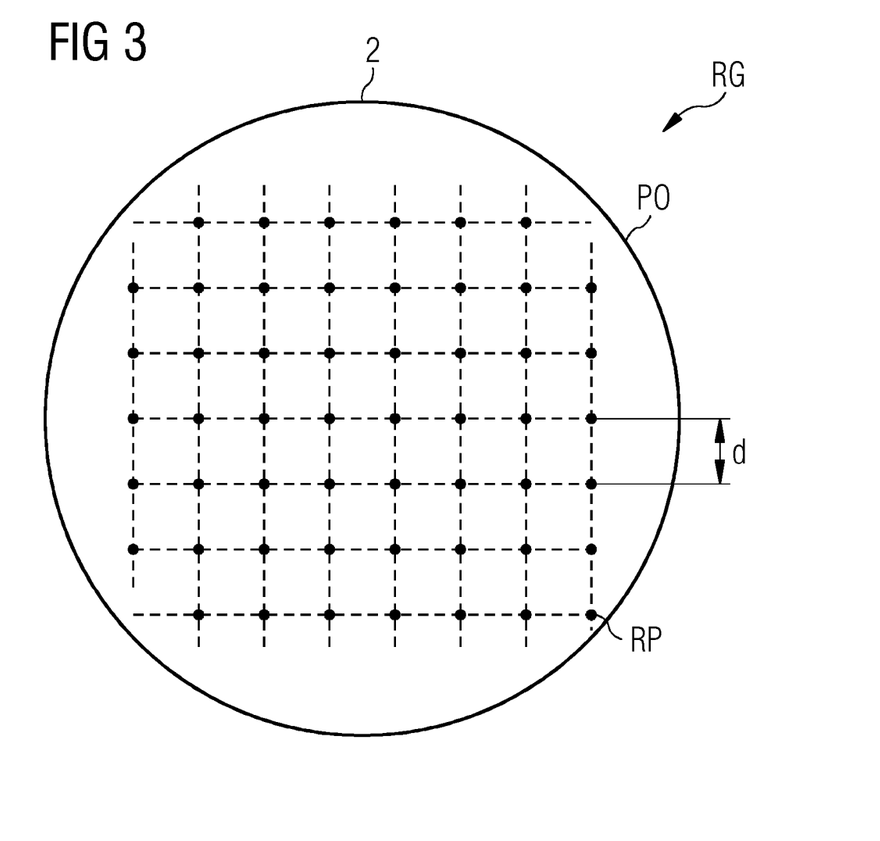
FIG. 3 shows a diagram to represent a reconstruction grid used in the method according to the invention.

For each measurement data set MDS determined, the evaluation unit 4 carries out an SAFT (Synthetic Aperture Focusing Technique) evaluation by using a common reconstruction grid RG within the test object 2 in order to calculate an SAFT evaluation result for each measurement data set MDS. An example of a reconstruction grid RG used is represented in FIG. 3. The evaluation unit 4 superposes the calculated SAFT evaluation results in order to calculate an orientation-independent defect display value for each point RP of the common reconstruction grid RG, as represented in FIG. 3. The reconstruction grid RG represented in FIG. 3 comprises a multiplicity of reconstruction points RP, which are arranged in a grid. The reconstruction grid RG is preferably three-dimensional. The RG may also be two-dimensional, if only a section plane of the component is measured and reconstructed, and the reconstruction points RP may be indicated by Cartesian coordinate points (x, y, z) or other coordinates, for example cylindrical or polar coordinates. The reconstruction grid RG may also be two-dimensional, in particular when only a section plane of the component, or test object, is measured and reconstructed. The reconstruction points RP are at a particular distance d from one another, as represented in FIG. 3. The reconstruction grid RG may also be irregular, and may for example contain a region with a smaller network, in which reconstruction is carried out in more detail. The reconstruction grid RG is a two- or three-dimensional virtual grid, which extends within the test object 2. The smaller the distance d between the reconstruction points RP of the reconstruction grid RG is, the greater the resolution obtained is, although the computation time for calculating the evaluation result increases. The distance d between the reconstruction points RP may, for example, lie in a range of from 0.5 to 1 mm.

In order to determine a measurement data set MDS, an ultrasound signal is respectively insonated by the test head 1 represented in FIG. 2 at various measurement points MP into the test object 2 with a particular insonation angle α of the measurement points MP, which angle is varied for each measurement data set MDS in order to determine the measurement data sets MDS. An SAFT evaluation is subsequently carried out by means of the evaluation unit 4 for each measurement data set MDS determined, by using the common reconstruction grid RG within the test object 2, in order to calculate an SAFT evaluation result for each measurement data set MDS. The calculated SAFT evaluation results are superposed in order to calculate an orientation-independent defect display value for each reconstruction point RP of the reconstruction grid RG. In one possible embodiment, the calculated SAFT evaluation results of the measurement data sets MDS determined may be weighted by the evaluation unit 4 in order to level the amplitude level before the superposition of the SAFT evaluation results. The superposed SAFT evaluation results may furthermore be rectified, and smoothed by lowpass filtering by the evaluation unit 4, in one possible embodiment.

As represented in FIG. 2, the measurement positions MP lie, for example, in a measurement network on the surface of the test object 2. For example, the distance between the measurement points MPi within the measurement network is constant, although the distance between the measurement points MP may also vary. For example, the distance between two measurement points MPi on the surface of the test object may be 2.5 mm. In the example represented in FIG. 2, the test object 2 is cylindrical; the test object 2 may, for example, be a turbine blade. When a measurement data set MDS is being recorded, the test head 1 for insonating the ultrasound signal into the test object 2 and for recording the echo ultrasound signals reflected back is moved continuously relative to the surface of the test object 2. In order to determine a measurement data set MDS, the ultrasound signal is insonated by means of the test head 1 at the various measurement points MP into the test object 2 with the insonation angle α respectively set to be constant for the determination of the measurement data set MDS. For example, a measurement data set MDS comprises N measurement data, which are recorded at N measurement positions MP. This is schematically represented in the table in FIG. 6. In this case, a first measurement data set MDS1 is recorded at N1 measurement positions for an insonation angle α1. Subsequently, the insonation angle α is set to a new insonation angle α2, and a further measurement data set MDS2 is recorded. In this way, for example, M measurement data sets may be generated for M different insonation angles α. The distances between the measurement points MP may be constant, although they may also vary. Furthermore, the number of measurement points within a measurement data set MDS may differ. The various measurement data sets MDS can be evaluated independently of one another by the evaluation unit 4 with the aid of an SAFT algorithm, the evaluation for all measurement data sets MDS being carried out at the same grid points of the reference grid RG represented in FIG. 3. If the exact positions of the measurement points, or of the measurement data, are not known, in one possible embodiment congruence of the positions of the reconstruction grid RG may be ensured by means of fine adjustment of the position of the measurement data, for example with the aid of the echo signal of an adjustment reflector, this signal being contained in all measurement data sets MDS. In this case, before the determination of the measurement data sets MDS, the measurement positions MP are adjusted accurately by means of the adjustment reflector with the aid of a reflected echo signal of the adjustment reflector. The adjustment is preferably carried out once, before the determination of the measurement data sets, in order to determine a position offset of test heads 1. The adjustment reflector therefore forms an aid for accurate determination of the measurement positions MP. The adjustment body, or adjustment reflector, may for example be a bore present at a particular position in the test object 2. The adjustment reflector is therefore formed by a defined inhomogeneity within the test object 2. By the evaluation unit 4, at each grid point RP of the reconstruction grid RG the SAFT evaluation results belonging to the various measurement data sets MDS are added in-phase.

Weighting of the SAFT evaluation results may in this case be carried out in order to compensate for different amplitude levels of the measurement data sets MDS. Furthermore, the sonic field may be jointly taken into account optionally when determining the SAFT evaluation results of the individual measurement data sets MDS. Furthermore, rectification or smoothing is optionally carried out after the superposition or fusion of the individual SAFT evaluation results.

Figure 4:
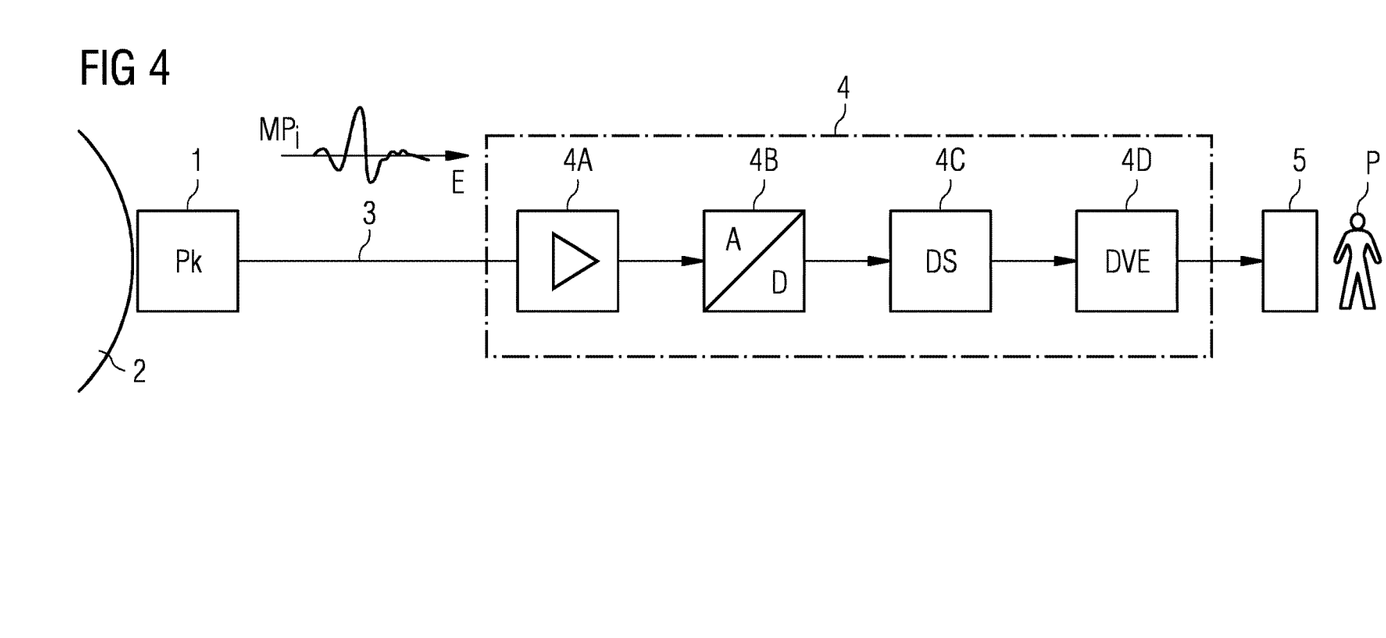
FIG. 4 shows a block diagram to represent an exemplary embodiment of the device according to the invention for detecting defects within a test object.
Figure 6:
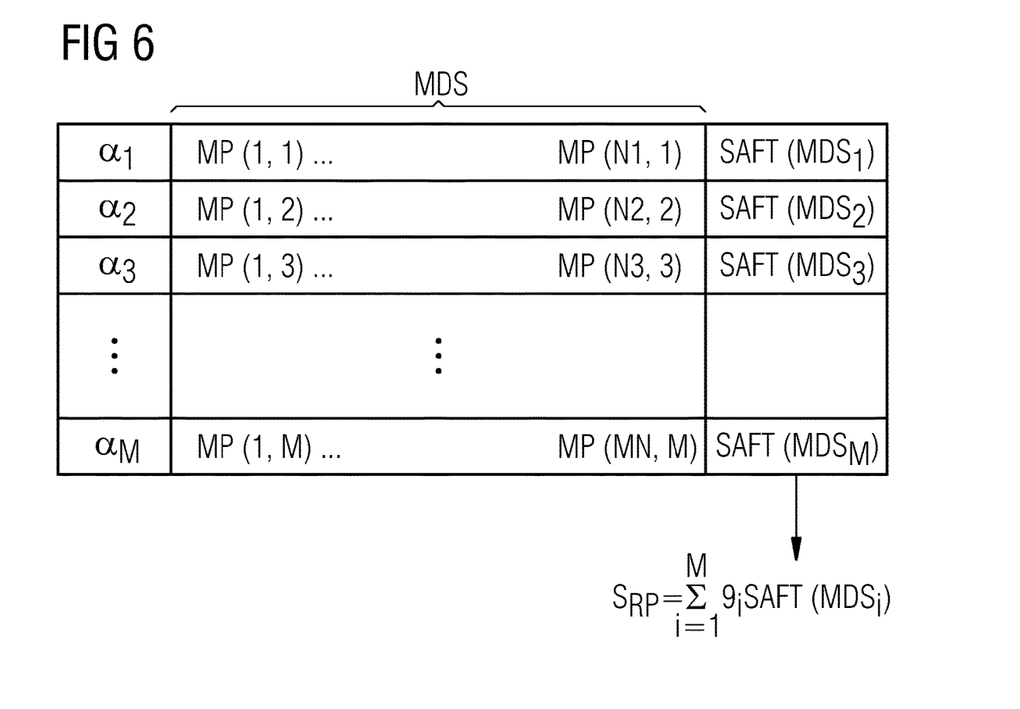
FIG. 6 shows a table to explain an exemplary embodiment of the method according to the invention for detecting defects within a test object.

FIG. 4 shows an exemplary embodiment of the device according to the invention for determining defects within a test object 2. In order to determine a measurement data sets MDS of the test object 2, by means of the test head 1 an ultrasound signal is insonated at the measurement points MP into the test object 2 with the insonation angle α currently set respectively for the determination of the measurement data set MDS. The analog echo ultrasound signals reflected back by the test object 2 at the various measurement points MP are recorded by the test head 1 and transmitted as a time-based signal for the respective measurement point MPi via the signal line 3 to the evaluation unit 4, as represented in FIG. 4. The received analog echo ultrasound signal for the respective measurement point MPi is first amplified by a signal amplifier 4A and digitized by an analog/digital converter 4B of the evaluation unit 4 to form measurement point echo data, which form the measurement data set MDS of the test object 2. The measurement data set MDS is subsequently stored in a data memory 4C of the evaluation unit 4 for further evaluation. For example, the data memory 4C comprises the data content represented in the table according to FIG. 6. The measurement data sets MDS buffered in the data memory 4C are evaluated and processed by a data processing unit 4D, for example a processor. For each measurement data set MDS, by using the common reconstruction grid RG within the test object 2, the processor 4D carries out an SAFT evaluation in order to calculate an SAFT evaluation result for the respective measurement data set MDS, as indicated in FIG. 6. Subsequently, the calculated SAFT measurement results SAFT(MDS) are superposed in order to calculate an orientation-independent defect display value $S_{RP}$ for each reconstruction point RP of the reconstruction grid RG, so that a defect display value $S_{RP}$ is calculated for each reconstruction point RP, as indicated in FIG. 6. In this case, the calculated SAFT evaluation results of the measurement data sets MDS determined are preferably weighted with weighting factors gi in order to level the amplitude level during the superposition of the SAFT evaluation results, as represented in FIG. 6:

$$S_{RP} = \sum_{i=1}^{M} g_i \text{SAFT}(\text{MDS}_i)$$

where $S_{RP}$ is the orientation-independent defect display value for a reconstruction point RP of the reconstruction grid RG, gi is an adjustable weighting factor, and SAFT(MDS) represents an SAFT evaluation result for a measurement data set MDS.

Figure 5:
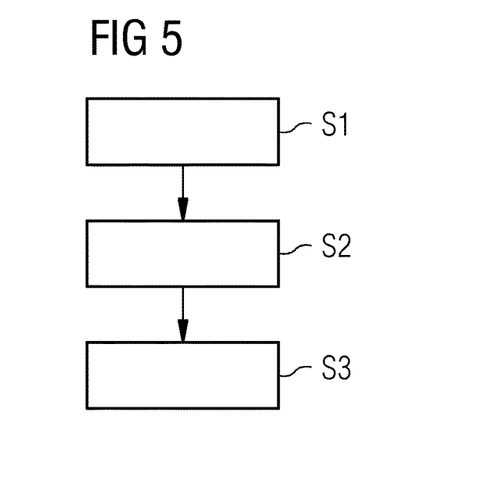
FIG. 5 shows a flow chart to represent an exemplary embodiment of the method according to the invention for detecting defects within a test object.

FIG. 5 shows a flow chart to represent an exemplary embodiment of the method according to the invention for detecting at least one defect within a test object 2.

In a step S1, a plurality of measurement data sets MDS of the test object 2 are initially determined, an ultrasound signal respectively being insonated by a test head 1 at various measurement points MP into the test object 2 with an insonation angle α in order to determine the measurement data set MDS, the insonation angle α being varied for each measurement data set MDS in order to determine the measurement data sets MDS.

In a further step S2, an SAFT evaluation is carried out for each measurement data set MDS determined, by using a common reconstruction grid RG within the test object 2 in order to calculate an SAFT evaluation result SAFT(MDS) for each measurement data set MDS.

Subsequently, in a step S3, the calculated SAFT evaluation results are superposed in order to calculate the orientation-independent defect display value $S_{RP}$ for each reconstruction point RP of the reconstruction grid RG. In step S3, weighting of the SAFT evaluation results may furthermore be carried out during the superposition. In a further step (not represented), the superposed SAFT evaluation results may be rectified, and/or smoothed by lowpass filtering.

In the method according to the invention, both single-oscillator test heads and group radiators, or phased-array test heads, may be used. The test object 2 may be inspected with different insonation angles α by various test heads, or by a phased-array test head, so that in this way a plurality of measurement data sets MDS, which consist of the measured time-based signals and the associated position information, are generated. In the method according to the invention, the scan network for the measurement data sets may differ, so that, if expedient, and a plurality of ultrasound scanners or ultrasound test heads may also be used simultaneously. The method represented in FIG. 5 may, for example, be configured as an application program on a data processing unit of the evaluation unit 4.

In the method according to the invention, the advantages of SAFT evaluation are exploited better, since possible defects existing within the test object 2 can be insonated by a plurality of measurements in a wide angle range. The method according to the invention leads to better lateral discrimination of defects and their size determination, as well as to higher signal-to-noise ratios SNR. In the method according to the invention, the detection of defects is carried out by means of SAFT evaluation independently of a defect orientation of the defect within the test object 2. Furthermore, in the method according to the invention, it is possible to use larger sonic transducers or test heads 1, which introduce more energy into the test object 2, or the component 2, while at the same time the sonic field has a small aperture angle. Single test heads and array test heads are equally suitable for the method according to the invention. The method according to the invention furthermore offers flexibility in the measurement, since the measurement data can be determined with a different measurement network. For example, a measurement network in the case of focused test heads, group radiators, may be selected or set more finely. If the SAFT evaluation results for the individual measurement data sets MDS are stored separately, the contributions of the various insonation angles α may furthermore be switched on and off, or selected, separately in the assessment of the evaluation results. Compared with conventional methods, the method according to the invention offers better determination of the fault or defect orientation, since in the method according to the invention it is possible to determine which insonation direction contributes most strongly to the respective evaluation result. Furthermore, the method according to the invention offers the possibility of the fusion of LW (longitudinal-wave) testing and TW (transverse-wave) testing. The ultrasound signal may be insonated into the test object 2 as a longitudinal wave LW or as a transverse wave TW in the method according to the invention.

The calculated defect display values $S_{RP}$ of the reconstruction grid RG are transmitted by the evaluation unit 4 represented in FIGS. 2 and 4 to the display 5, and displayed there to the tester P two-dimensionally in sectional views or three-dimensionally.

In one possible embodiment, the calculated defect display values $S_{RP}$ of the examined test object 2 are compared by the evaluation unit 4 with setpoint values of a stored model of the test object 2 to be examined, in order to calculate difference values ΔS, a defect of the test object 2 being indicated or displayed when predetermined tolerance threshold values are exceeded. In one possible embodiment of the method according to the invention, a test object 2 identified as defective is then automatically rejected or reprocessed. The method according to the invention is suitable for any desired test objects 2, for example rotationally symmetrical forged parts, rotor parts on a gas turbine, cylinders and the like. The test object 2 may furthermore have any desired shape, for example round, cylindrical, but also square or polygonal. The method according to the invention takes into account various insonation angles α and at the same time is flexible in terms of the measurement network. In the method according to the invention, a plurality of scans may furthermore be carried out in the depth of a test object 2 to be examined.

The invention claimed is:
1. A method for detecting at least one defect within a test object, the method comprising the steps:
    (a) determining a plurality of measurement data sets by insonating an ultrasound signal into the test object respectively at various measurement points such that at a first measurement point of the various measurement points a first insonation angle for a first measurement data set of the plurality of measurement data sets is different from a second insonation angle at the first measurement point for a second measurement data set of the measurement data sets,
    (b) carrying out a Synthetic Aperture Focusing Technique (SAFT) evaluation for each measurement data set, wherein the evaluation is determined by using a common reconstruction grid within the test object for calculating the SAFT evaluation result for each measurement data set;
    (c) superposing the calculated SAFT evaluation results, in order to calculate an orientation-independent defect display value for each reconstruction point of the reconstruction grid; and
    (d) detecting the at least one defect within the test object based on the calculated orientation-independent defect display value.

2. The method as claimed in claim 1, further comprising weighting the calculated SAFT evaluation results of the measurement data sets evaluated and determined in order to level the amplitude level before the superposition of the SAFT evaluation results.

3. The method as claimed in claim 2, further comprising separately storing the SAFT evaluation results, calculated for the various insonation angles of the various measurement data sets, and selecting the SAFT evaluation results for the superposition with the aid of the insonation angle.

4. The method as claimed in claim 1, further comprising rectifying and smoothing the superposed SAFT evaluation results by lowpass filtering.

5. The method as claimed in claim 1, wherein the measurement positions lie in a measurement network on the surface of the test object.

6. The method as claimed in claim 1, further comprising, before the determination of the measurement data sets, adjusting the measurement positions by aid of a reflected echo signal of an adjustment reflector.

7. The method as claimed in claim 1, wherein the insonating of the ultrasound signal is performed by a single-oscillator test head or by a group radiator test head, wherein the isonating is performed at the various measurement points into the test object and the respective insonation angle is set for the determination of the measurement data set; and the method further comprises:
    amplifying and subsequently digitizing analog echo ultrasound signals reflected by the test object for the various measurement points for digitizing the signals to form measurement point echo data, which form the measurement data set of the test object.

8. The method as claimed in claim 7, further comprising moving the single-oscillator test head or the group radiator test head for insonating the ultrasound signals and for recording the echo ultrasound signals continuously relative to the surface of the test object.

9. The method as claimed in claim 1, further comprising:
    insonating the ultrasound signal into the test object as a longitudinal wave and/or a transverse wave.

10. The method as claimed in claim 1, further comprising displaying the calculated defect display values of the reconstruction grid to a tester two-dimensionally in sectional views or three-dimensionally on a display.

11. The method as claimed in claim 1, further comprising comparing the calculated defect display values of the examined test object respectively with setpoint values of a stored model of the test object to be examined, for calculating difference values which indicate a defect of the test object when predetermined tolerance threshold values are exceeded.

12. The method as claimed in claim 11, further comprising automatically rejecting a test object identified as defective.

13. A method according to claim 1, wherein the insonating angle for all measurement points in a measurement data set is constant.

14. A device for detecting at least one defect within a test object, the device comprising:
    at least one test head configured for insonating into the test object an ultrasound signal at various measurement points,
    wherein in order to determine the measurement data sets, the device is configured such that at a first measurement point of the various measurement points the ultrasound signal is respectively insonated at a first insonation angle into the test object for generating a first measurement data set of a plurality of measurement data sets, and for a second measurement data set of the plurality of measurement data sets the ultrasound is insonated at the first measurement point at a second insonation angle different from the first insonation angle; and
    an evaluation unit configured to carry out an Synthetic Aperture Focusing Technique (SAFT) evaluation for each measurement data set determined, the evaluation unit is configured to use a common reconstruction grid within the test object for calculating an SAFT evaluation result for each measurement data set, the evaluation unit is configured to superpose the calculated SAFT evaluation results for calculating an orientation-independent defect display value for each reconstruction point of the common reconstruction grid,
    wherein the device is configured to detect the at least one defect within the test object based on the calculated orientation-independent defect display value.

15. The device as claimed in claim 14, wherein the evaluation unit is configured to weight the calculated SAFT evaluation results of the measurement data sets determined, in order to level the amplitude level before the superposition of the SAFT evaluation results.

16. The device as claimed in claim 14, wherein the test head is configured to move continuously relative to a surface of the test object in order to determine the measurement data sets.

* * * * *